United States Patent [19]

Ager et al.

[11] 4,389,528

[45] * Jun. 21, 1983

[54] TRIALKYLAMINE/SULFUR DIOXIDE CATALYZED SULFENYLATION OF CARBAMATES

[75] Inventors: John W. Ager; Maurice J. C. Harding, both of Princeton; Charles E. Hatch, III, Pennington, all of N.J.

[73] Assignee: FMC Corporation, Philadelphia, Pa.

[*] Notice: The portion of the term of this patent subsequent to May 11, 1999, has been disclaimed.

[21] Appl. No.: 350,792

[22] Filed: Feb. 22, 1982

Related U.S. Application Data

[63] Continuation-in-part of Ser. No. 202,526, Oct. 31, 1980, Pat. No. 4,329,293.

[51] Int. Cl.³ .......................................... C07D 307/86
[52] U.S. Cl. ................................................ 549/470
[58] Field of Search ........................................ 549/470

[56] References Cited

U.S. PATENT DOCUMENTS 4,329,293  5/1982  Ager et al. ...................... 549/470

Primary Examiner—John M. Ford
Assistant Examiner—Bernard Dentz
Attorney, Agent, or Firm—Robert L. Andersen; H. Robinson Ertelt

[57] ABSTRACT

An improved process for sulfenylating carbofuran in the presence of a solvent and acid acceptor with a di-substituted aminosulfenyl halide, in which the reaction is conducted in the presence of a catalytic amount of a complex of a lower alkylamine and sulfur dioxide, is disclosed and exemplified.

6 Claims, No Drawings

TRIALKYLAMINE/SULFUR DIOXIDE CATALYZED SULFENYLATION OF CARBAMATES

This application is a continuation in part of allowed U.S. application Ser. No. 202,526, filed Oct. 31, 1980, the disclosure of which is incorporated herein by Reference, now U.S. Pat. No. 4,329,293.

The present invention relates to a process for sulfenylating carbamates with a sulfenyl halide in the presence of a solvent and a hydrogen halide acceptor. More particularly the invention relates to aminosulfenylation of carbofuran with certain disubstituted aminosulfenyl halides in the presence of a catalytic amount of a complex of sulfur dioxide and a trialkylamine.

The reaction of an aminosulfenyl halide with a carbamate in the presence of a solvent and an acid acceptor is known. For example U.S. Pat. No. 4,006,231 describes the preparation of aminothio derivatives of carbofuran, the common name for 2,3-dihydro-2,2-dimethyl-7-benzofuranyl methylcarbamate, by reacting together carbofuran and an aminosulfenyl halide in pyridine, the pyridine serving as solvent and acid acceptor for the reaction, the reaction taking place over a period of about 18 hours. Similarly, U.S. Pat. No. 4,108,991 discloses a comparable reaction in which aldicarb, the common name for 2-methyl-2-methylthiopropanal O-(methylcarbamoyl)oxime, is reacted with an aminosulfenyl halide in the presence of pyridine. U.S. Pat. No. 3,847,951 discloses that arylthio or alkylthio carbamates may be prepared by the reaction of an alkylsulfenyl or arylsulfenyl halide and carbofuran in the presence of an amine base, such as triethylamine, pyridine, or quinuclidine, and an aprotic organic solvent such as dimethylformamide.

U.S. Pat. No. 3,980,673 teaches, for the reaction of an arylsulfenyl chloride with carbofuran, that one may employ as solvents an ether such as diethyl ether, dioxane, or tetrahydrofuran, a hydrocarbon such as benzene, or chlorinated hydrocarbons such as chloroform or chlorobenzene. This patent also discloses, for aryl sulfenylation, that a tertiary organic base such as triethylamine is the preferred acid-binding agent. U.S. Pat. No. 3,997,549 teaches reacting the reaction product of sulfuryl chloride and 4-t-butylbenzenethiol in pyridine with carbofuran to produce 2,3-dihydro-2,2-dimethyl-7-benzofuranyl (4-t-butylphenylthio)(methyl)carbamate.

Unless otherwise specified in the specification and claims which follow, the term "lower" as applied to an aliphatic group such as alkyl means a group having 1 to 6, preferably 1 to 4 carbon atoms, and the terms "halo" or "halogen" include bromine, chlorine or fluorine.

The present invention provides an improved process for sulfenylating carbofuran with certain disubstituted aminosulfenyl halides in the presence of a solvent and an acid acceptor to produce a corresponding sulfenylated derivative in which the free hydrogen has been replaced by a disubstituted aminosulfenyl group, the sulfenylation reaction being conducted in the presence of a catalytic amount of a complex of sulfur dioxide and a trialkylamine.

The present invention is applicable to reaction of carbofuran, a carbamate of the general formula $R^1OOCNHCH_3$, in which $R^1$ is a 2,3-dihydro-2,2-dimethyl-7-benzofuranyl group, with a sulfenyl halide of the formula $R^3SX$ to produce a corresponding sulfenylated derivative.

The general reaction is illustrated by equation A:

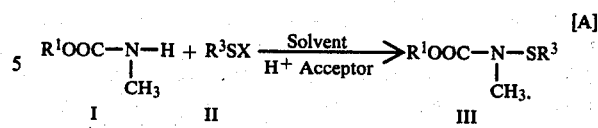

In the present invention suitable sulfenyl halides are those of formula II, in which X is a halogen atom such as chlorine, bromine or fluorine, preferably chlorine or bromine and $R^3$ is a disubstituted amino group of the formula $R^7R^8N-$ in which: (1) one of $R^7$ and $R^8$ is a lower alkyl group, and the other is a group of the formula $-CH_2CO_2R^9$ in which $R^9$ is a lower alkyl group or (2) both of $R^7$ and $R^8$ are like groups of the formula $-CH_2CO_2R^9$ in which $R^9$ is a lower alkyl group, the latter being preferred.

The reaction is conducted in the presence of a solvent and an acid acceptor and in the presence of a catalytic amount of a complex of sulfur dioxide ($SO_2$) and a trialkylamine (TA).

The catalytic complex employed in this invention, sometimes referred to by the symbol $TA.SO_2$, generally contains substantially equimolar amounts of the trialkylamine and sulfur dioxide, but excess amounts of the amine or sulfur dioxide may be present in the reaction mixture if desired.

Suitable trialkylamines include compounds of the formula $R^4R^5R^6N$ in which $R^4$, $R^5$ and $R^6$ are alkyl groups of 1 to 4, preferably 1 to 2, carbon atoms. This includes amines such as triethylamine, trimethylamine and mixed trialkylamines. Triethylamine is the preferred amine.

The complex of a trialkylamine and sulfur dioxide can be formed in several ways. It can be prepared separately by passing sulfur dioxide through a solution of the trialkylamine in an appropriate solvent, for example hexane. The resulting product may then be used without isolation of the complex in Reaction A. The sulfur dioxide and the trialkylamine may also be added separately to a mixture of carbamate and sulfenyl halide and an appropriate solvent. Additionally, the sulfur dioxide may be formed in situ during preparation of the sulfenyl halide, by reacting an appropriate bis-disulfide with sulfuryl chloride, as illustrated in Reaction B

The resulting reaction mixture, containing $SO_2$ in solution, can then be combined with the trialkylamine to form the $TA.SO_2$ complex and the resulting mixture used without isolation in Reaction A. Also, the carbamate, acid acceptor and trialkylamine may be added to the product of Reaction B, so that the complex actually forms in situ during Reaction A. It is preferable to employ excess, preferably at least a 10 percent molar excess, of sulfenyl halide to carbamate in the reaction.

The amount of complex employed in the reaction of the sulfenyl halide with the carbamate can be varied, but must be at least an amount sufficient to catalyze the reaction, i.e. a catalytic amount. While the precise amounts needed may vary with the particular reactants, in general at least about 0.01 mole of catalyst complex per mole of carbamate should be present. About 0.03 up to about 0.3 mole per mole carbamate has been found to substantially improve reaction time, product yield, and product purity, but larger amounts, for example up to about 0.6 mole per mole of carbamate may be employed if desired.

Solvents suitable for the reaction of the sulfenyl halide with the carbamate include aromatic hydrocarbons of 6 to 10 carbon atoms such as benzene or toluene, halogenated aliphatic hydrocarbons of 1 to 4 carbon atoms such as methylene chloride, saturated aliphatic hydrocarbons of 5 to 10 carbon atoms, preferably 5 to 8 carbon atoms, such as petroleum ether, ligroin, heptane, hexane, or octane, ethers such as tetrahydrofuran, polar aprotic solvents such as dimethylformamide (DMF) or dimethylsulfoxide (DMSO), or aromatic nitrogen containing solvents such as pyridine. Most preferably, saturated aliphatic hydrocarbons such as hexane or heptane are preferred because unreacted carbofuran can be recovered by filtration due to its relatively low solubility in the solvent.

An acid or hydrogen halide acceptor is present to aid the reaction. Suitable acid acceptors are well known in this art. Preferred acid acceptors include pyridine or lower alkylamines such as triethylamine, but other tertiary or aromatic organic amines can be employed. The amount of acid acceptor employed in the reaction should at least be sufficient to take up or neutralize the amount of hydrogen halide formed during the course of the reaction. Thus from about 1 to about 2 molar equivalents of acid acceptor should be employed per mole of carbamate. Preferably an equimolar amount or slight molar excess of acid acceptor is utilized, for example about 1.0 to 1.75 molar equivalents of acid acceptor per mole of carbamate, preferably 1.0 to about 1.5. If a tertiary amine is used as the acid acceptor and complexing agent, sufficient amine must be present to take up or neutralize the hydrogen halide formed and to form a catalytic amount of the sulfur dioxide/alkylamine complex described above.

The reaction between the sulfenyl halide and the carbamate is suitably run at room temperature, but this temperature may vary, for example between 0° C. and 50° C.

The preferred embodiment of the invention is one in which a disubstituted aminosulfenyl chloride is prepared in accordance with reaction B to form a reaction mixture containing sulfur dioxide.

The equation for the reaction is as follows:

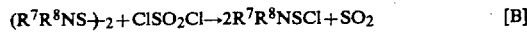

The sulfur dioxide is formed in situ and remains in solution due to its solubility in the sulfenyl chloride. The solvent for the reaction is one in which the sulfenyl chloride is soluble, for example hexane or dimethylformamide (DMF). The reaction product containing the sulfenyl halide and SO$_2$ is then combined with sufficient triethylamine (TEA) to form a 1:1 complex with the sulfur dioxide (TEA SO$_2$), an appropriate carbamate, and sufficient acid acceptor to remove the by product hydrogen chloride. This procedure permits the preparation of the sulfenyl halide and the reaction of the sulfenyl halide with the carbamate to be performed in successive steps in a single reactor without isolation of intermediates. Thus the best mode for conducting the reaction is to form the sulfenyl chloride and SO$_2$ in situ and to add to the resulting reaction mixture appropriate amounts of the carbamate then triethylamine, the triethylamine acting as agent for the complexing of sulfur dioxide and also as an acid acceptor.

It is also possible to prepare the disulfide starting material in situ in accordance with Reaction C:

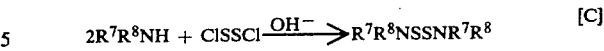

Thus all three steps may be conducted in a single solvent in a single reactor without isolation of intermediates.

The following examples will further illustrate the practice of the present invention.

EXAMPLE 1

Synthesis of Diethyl-[((((2,3-dihydro-2,2-dimethyl-7-benzofuranyl)oxy)carbonyl)methylamino)thio]iminobis[acetate]

Step A Synthesis of Iminodiacetic Acid Diethyl Ester

A stirred solution of 931.0 grams (7.0 moles) of iminodiacetic acid and 1.0 ml of N,N-dimethylformamide in 5.25 liters of ethanol was cooled to 12° C. During a 1.5 hour period 2,100 grams (17.65 moles) of thionyl chloride was added dropwise to the cold solution. After complete addition the reaction mixture was heated at 60° C. for three hours, at reflux for two hours, then allowed to stand at room temperature for approximately 16 hours. The mixture was distilled at reduced pressure to remove 4.0 liters of ethanol leaving a liquid residue. The residue was dissolved in 4.0 liters of methylene chloride, then extracted with 3.5 liters of an aqueous 20% sodium carbonate solution. The aqueous extract was back washed with 1.0 liter of methylene chloride. The organic phases were combined, washed with 1.0 liter of water and evaporated under reduced pressure to leave a liquid. The liquid was purified by distillation under reduced pressure to yield 880.0 grams of iminodiacetic acid diethyl ester (b.p. 123° C./4.5 mmHg).

Step B Synthesis of Dithiobis(imino)tetrakis[acetic acid], tetraethyl ester

Under a dry nitrogen atmosphere a stirred solution of 1,021 grams (5.4 moles, a combination of several samples prepared by the method of Step A) of iminodiacetic acid diethyl ester in 1.945 liters of n-hexane and 300.0 ml of tetrahydrofuran was cooled to 0° C. Triethylamine (547.0 grams, 5.4 moles) was added to the cold reaction mixture. After complete addition a solution consisting of 400.0 grams (2.96 moles) sulfur monochloride in 1.55 liters of n-hexane was added to the cold mixture during a two hour period. An additional 4.0 liters of n-hexane and 500.0 ml of tetrahydrofuran was added to aid stirring. After complete addition the reaction mixture was warmed to room temperature and stirred for approximately 16 hours. Water (3.0 liters) was added to the mixture and the total stirred vigorously for 15 minutes. The stirring was stopped and the phases separated to give an organic phase (1) and an aqueous phase (2). The organic phase (1) was washed with water, dried over anhydrous magnesium sulfate and filtered. The filtrate was evaporated under reduced pressure to yield 415.0 grams of dithiobis(imino)tetrakis[acetic acid], tetraethyl ester as an oil. The aqueous phase (2) was extracted with two 1.0 liter portions of toluene. The extracts were combined, dried over anhydrous magnesium sulfate and filtered. The filtrate was evaporated under reduced pressure to yield an additional 499.0 grams of product.

Step C Synthesis of [((((2,3-dihydro-2,2-dimethyl-7-benzofuranyl)oxy)carbonyl)methylamino)thio]iminobis[acetate]

During a 30 minute period 67.5 grams (0.5 mole) of sulfuryl chloride was added dropwise to a stirred solution of 255.0 grams (0.58 mole) of dithiobis(imino)tetrakis[acetic acid], tetraethyl ester in 500.0 ml of methylene chloride, maintaining a temperature of about 20° C. After complete addition the mixture was stirred for 25 minutes, at which time 221.0 grams (1.0 mole) of carbofuran was added. After complete addition 160.0 grams (1.58 moles) of triethylamine was added during a 30 minute period. The reaction temperature was maintained at about 30° C. throughout the addition. The resulting mixture was stirred at room temperature for three hours then cooled to about 10° C. Water (400.0 ml) was added to the mixture and the total stirred for a short period. The stirring was stopped and the resulting phases separated. The organic phase was washed with two 100.0 ml portions of water then evaporated under reduced pressure to yield 468.0 grams of a viscous oil. High performance liquid chromatographic analysis (HPLC) of the oil indicated 90.0% [((((2,3-dihydro-2,2-dimethyl-7-benzofuranyl)oxy)carbonyl)methylamino)thio]iminobis[acetate] and 4.4% carbofuran.

The attached table shows additional examples for preparing the compound of Example 1.

TABLE I

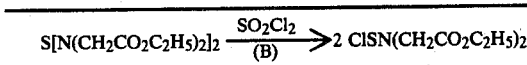

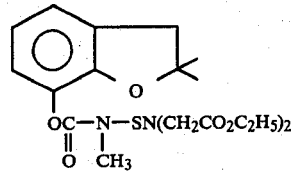

| Example | (A) moles | (B) moles | (C) moles | (D) moles | Product (E) grams | HPLC Analysis[a] (E) % | (D) % |
|---|---|---|---|---|---|---|---|
| 2 | 0.05 | 0.05 | 0.16 | 0.10 | 36.0 | 74.9 | 9.7 |
| 3 | 0.58 | 0.50 | 1.58 | 1.0 | 452.0 | 86.8 | 1.9 |
| 4 | 0.58 | 0.50 | 1.58 | 1.0 | 468.0 | 90.0[b] | 4.4 |
| 5 | 1.01 | 0.87 | 2.76 | 1.7 | 890.0 | 82.8 | 2.6 |
| 6 | 2.84 | 1.46 | 7.78 | 4.7 | 2164.0 | 84.5 | 3.9 |

[a]HPLC % based on Example 3 product mixture as 90.0% desired product.
[b]HPLC % based on 2,3-dihydro-2,2-dimethyl-7-benzofuranyl [(dibutylamino)thio]methylcarbamate, also known by the common name carbosulfan as the internal standard.
[c]Triethylamine

We claim:
1. A process for preparing a compound of the formula

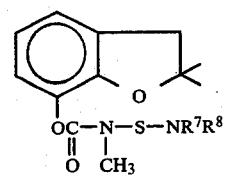

which comprises, reacting carbofuran with a disubstituted aminosulfenyl halide of the formula $R^3SX$ in the presence of a solvent and acid acceptor in the presence of a catalytic amount of a complex of sulfur dioxide and a trialkylamine of the formula $R^4NR^5R^6$ wherein each of $R^4$, $R^5$ and $R^6$ is a lower alkyl group, wherein
 (a) X is a halogen atom and $R^3$ is $-NR^7R^8$;
 (b) one of $R^7$ and $R^8$ is a group of the formula $-CH_2CO_2R^9$ wherein $R^9$ is a lower alkyl group and, the other of $R^7$ and $R^8$ is a lower alkyl group or a group of the formula $-CH_2CO_2R^9$.

2. The process of claim 1 in which each of $R^4$, $R^5$ and $R^6$ is an alkyl group of 1 to 2 carbon atoms.

3. The process of claim 1 wherein the trialkylamine is triethylamine.

4. The process of claim 1 wherein said complex comprises an equimolar amount of sulfur dioxide and triethylamine.

5. The process of claim 1 wherein there is employed at least 0.01 moles of sulfur dioxide and triethylamine or the complex thereof per mole of carbofuran, and wherein said aminosulfenyl halide is a sulfenyl chloride.

6. The process improvement of claim 1 in which $R^7$ and $R^8$ are both groups of the formula $-CH_2CO_2C_2H_5$.